US011992526B2

(12) United States Patent
Tarpey

(10) Patent No.: US 11,992,526 B2
(45) Date of Patent: May 28, 2024

(54) RABIES VIRUS VACCINE

(71) Applicant: Intervet Inc., Madison, NJ (US)

(72) Inventor: Ian Tarpey, St. Ives (GB)

(73) Assignee: Intervet Inc., Rahway, NJ (US)

( * ) Notice: Subject to any disclaimer, the term of this patent is extended or adjusted under 35 U.S.C. 154(b) by 0 days.

(21) Appl. No.: 16/759,868

(22) PCT Filed: Nov. 5, 2018

(86) PCT No.: PCT/EP2018/080086
§ 371 (c)(1),
(2) Date: Apr. 28, 2020

(87) PCT Pub. No.: WO2019/086645
PCT Pub. Date: May 9, 2019

(65) Prior Publication Data
US 2020/0345832 A1     Nov. 5, 2020

Related U.S. Application Data

(60) Provisional application No. 62/581,955, filed on Nov. 6, 2017.

(51) Int. Cl.
*A61K 39/205* (2006.01)
*A61K 39/00* (2006.01)
*A61P 31/14* (2006.01)

(52) U.S. Cl.
CPC ............ *A61K 39/205* (2013.01); *A61P 31/14* (2018.01); *A61K 2039/5256* (2013.01); *A61K 2039/552* (2013.01); *C12N 2760/20034* (2013.01); *C12N 2760/20071* (2013.01); *C12N 2770/36143* (2013.01); *C12N 2770/36171* (2013.01)

(58) Field of Classification Search
None
See application file for complete search history.

(56) References Cited

U.S. PATENT DOCUMENTS

| 7,208,161 | B1 * | 4/2007 | Murphy | ............... C07K 14/005 |
| | | | | 424/199.1 |
| 8,460,913 | B2 | 6/2013 | Kamrud et al. | |
| 8,795,681 | B2 * | 8/2014 | Wu | ..................... A61K 39/0225 |
| | | | | 424/199.1 |
| 9,314,519 | B2 | 4/2016 | Qiao et al. | |
| 9,441,247 | B2 | 9/2016 | Rayner et al. | |
| 2014/0271829 | A1 * | 9/2014 | Lilja | ....................... A61K 39/25 |
| | | | | 424/450 |

FOREIGN PATENT DOCUMENTS

| CN | 101355960 A | 1/2009 | |
| CN | 105517569 A | 4/2016 | |
| JP | 2007537761 A | 12/2007 | |
| JP | 2014500013 A | 1/2014 | |
| WO | 2005113782 A1 | 12/2005 | |
| WO | 2007047749 A1 | 4/2007 | |
| WO | WO-2012061815 A2 * | 5/2012 | ........... A61K 39/205 |
| WO | 2013138776 A1 | 9/2013 | |
| WO | WO-2013138776 A1 * | 9/2013 | ........... A61K 39/205 |
| WO | 2015024665 A1 | 2/2015 | |

OTHER PUBLICATIONS

Stardubova et al., "Creation of DNA Vaccine Vector Based on Codon-Optimized Gene of Rabies Virus Glycoprotein (G Protein) with Consensus Amino Acid Sequence," Molecular Biology, vol. 50, No. 2: 328-331 (Year: 2016).*
Bernstein, Di, et al, Randomized, double-blind, Phase 1 trial of an alphavirus replicon vaccine for cytomegalovirus in CMV seronegative adult volunteers, Vaccine, 2009, 484-493, vol. 28, No. 2.
Bredenbeek, Peter J. et al., Sindbis Virus Expression Vectors: Packaging of RNA Replicons by Using Defective Helper RNAs, Journal of Virology, 1993, 6439-6446, 67(11).
Cox, James H. et al., Rabies Virus Glycoprotein II. Biological and Serological Characterization, Infection and Immunity, 1977, 754-759, 16(3).
Dietzschold, Bernhard et al., New Developments in the Pre- and Post-Exposure Treatment of Rabies, Crit Rev Immunol, 1991, 427-439, 10.
International Search Report for PCT/EP2018/080086 dated Mar. 1, 2019, 15 pages.
Kamrud, K.I. et al., Development and characterization of promoterless helper RNAs for the production of alphavirus replicon particle, Journal of General Virology, 2010, 1723-1727, 91(Pt 7).
Liljestrom, P. et al., A new generation of animal cell expression vectors based on the semliki forest virus replicon, Biotechnology, 1991, pp. 1356-1361, 9.
Loy, JD et al, Development and evaluation of a replicon particle vaccine expressing the E2 glycoprotein of bovine viral diarrhea virus (BVDV) in cattle, Virology Journal, 2013, 35, vol. 10, No. 1.
Lundstrom, K, Replicon RNA Viral Vectors as Vaccines, Vaccines, 2016, 39, vol. 4, No. 4.
Mähl, Philippe et al., Twenty year experience of the oral rabies vaccine SAG2 in wildlife: a global review, Veterinary Research, 2014, 1-17, 45(1):77.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Robinson, Laura E. et al., Rabies, Semin. Vet. Med. Surg. (Small Anim.), 1991, 203-211, 6(3).
Schultz-Cherry, S et al, Influenza Virus (A/HK/156/97) Hemagglutinin Expressed by an Alphavirus Replicon System Protects Chickens against Lethal Infection with Hong Kong-Origin H5N1 Viruses, Virology, 2000, 55-59, vol. 278, No. 1.
Vander Veen, RL et al, Alphavirus replicon vaccines, Animal Health Research Reviews, 2012, 1-9, vol. 13, No. 1.

(Continued)

*Primary Examiner* — M Franco G Salvoza
(74) *Attorney, Agent, or Firm* — David J. Kerwick

(57) ABSTRACT

The present invention provides a vaccine for rabies virus and methods of making and using the vaccine alone, or in combinations with other protective agents.

18 Claims, No Drawings

Specification includes a Sequence Listing.

(56) References Cited

OTHER PUBLICATIONS

Vander Veen, RL et al, Safety, immunogenicity, and efficacy of an alphavirus replicon-based swine influenza virus hemagglutinin vaccine, Vaccine, 2012, 1944-1950, vol. 30, No. 11.
Sedova, E.S. et al., New recombinant rabies vaccines, BIOpreparations. Prevention, Diagnosis, Treatment, 2016, 219-228, 16(4).
Sedova, E.S. et al., New recombinant rabies vaccines, BIOpreparations. Prevention, Diagnosis, Treatment, 2016, 219-228, 16(4)—English Translation.
Jas, D., et al, Three-year duration of immunity in cats vaccinated with a canarypox-vectored recombinant rabies virus vaccine, Vaccine, 2012, 6991-6996, 30 (2012).
USDA Summary of Studies Supporting USDA Product Licensure, Boehringer Ingelheim Animal Health USA Inc.; Rabies Vaccine, Live Canarypox Vector; Complied May 17, 2019, 5 pages.
Saxena, Sonal et al., Induction of immune responses and protection in mice against rabies using a self-replicating RNA vaccine encoding rabies virus glycoprotein, Veterinary Microbiology, 2009, 36-44, 136.
Thompson, Joseph M. et al., Mucosal and systemic adjuvant activity of alphavirus replicon particles, PNAS, 2006, 3722-3727, 103(10).
Saxena, Sonal et al., A sindbis virus replicon-based DNA vaccine encoding the rabies virus glycoprotein elicits immune responses and complete protection in mice from lethal challenge, Vaccine, 2008, 6592-6601, 26.

* cited by examiner

SEQUENCE LISTING

<160> NUMBER OF SEQ ID NOS: 4

<210> SEQ ID NO 1
<211> LENGTH: 1575
<212> TYPE: DNA
<213> ORGANISM: Artificial Sequence
<220> FEATURE:
<223> OTHER INFORMATION: codon optimized for humans

<400> SEQUENCE: 1

```
atggtgccgc aggctctcct gtttgtcccc cttctggtct ttccattgtg ttttgggaaa      60
ttccctatct acacaattcc ggacaagttg ggaccctgga gcccaattga cattcatcat     120
ctcagctgcc cgaacaattt ggtcgtggag gacgaaggat gcaccaacct gtcggggttc     180
tcctacatgg aattgaaagt cggatacatc agtgccatta gatgaacgg gttcacttgc      240 acaggcgtcg tgactgaagc tgagacatac actaacttcg tgggatatgt cactaccact     300
ttcaaaagaa agcatttccg ccctactcct gatgcttgta gggccgcata caactggaag     360
atggccggtg acccccagata tgaggaatca cttcacaatc cgtaccctga ctaccactgg     420
cttcggactg tcaaaaccac caaggagtca ctcgtgatca ttagtccaag tgtggctgat     480
cttgacccat acgaccggtc acttcactca cgggtgttcc cggggggggaa ttgctctggt     540 gtcgcagtgt cgtcaaccta ctgctccaca aaccacgatt acacctttg gatgccagaa     600
```

-continued aatcctcggc ttggtatgtc atgtgacatt ttcaccaatt ctcgggggaa gagggcttcc 660
aaagggtctg aaacttgcgg ctttgtcgat gagcggggct tgtataagtc acttaaaggt 720
gcttgcaaac tcaagctttg tggtgtcttg ggattgagat tgatggatgg aacttgggtc 780
gcaatgcaga cttctaacga aaccaaatgg tgccctcccg gacagcttgt gaatttgcat 840
gactttcgct ctgacgaaat tgagcatctt gtcgtcgagg agttggtcaa gaagcgggaa 900
gagtgtctgg atgctttgga atcaatcatg accaccaagt cagtgtcttt cagacggctc 960
tcacatctta ggaaattggt gccaggtttt ggaaaagcat ataccatttt caacaagacc 1020
cttatggaag ccgatgctca ctacaagtct gtcaggactt ggaatgagat catcccgtct 1080
aaagggtgtc ttagggtcgg agggagatgt catcctcatg tcaacggagt ctttttcaat 1140
ggtatcattc ttggacctga cggaaatgtc cttatccctg agatgcaatc ttccctcctc 1200
cagcaacaca tggaacttct tgtctcatcg gtcatccccc ttatgcaccc cctggctgac 1260
ccatcaaccg tgttcaagaa cggtgacgag gcagaggatt ttgtcgaggt ccaccttccc 1320
gatgtgcatg aacggatctc tggtgtcgac cttggactcc ctaactgggg aaagtatgtc 1380
cttctgtcgg caggagccct gactgccttg atgttgatta tcttcctgat gacttgttgg 1440
aggagagtca atcggtcgga gccaacacaa cataatctca gaggaacagg aagggaggtg 1500
tcagtcacac cccaaagcgg gaagatcatt tcgtcttggg agtcatacaa gagcggaggt 1560
gaaaccggac tgtga 1575

<210> SEQ ID NO 2
<211> LENGTH: 524
<212> TYPE: PRT
<213> ORGANISM: Rabies virus

<400> SEQUENCE: 2

Met Val Pro Gln Ala Leu Leu Phe Val Pro Leu Leu Val Phe Pro Leu
1 5 10 15

Cys Phe Gly Lys Phe Pro Ile Tyr Thr Ile Pro Asp Lys Leu Gly Pro
20 25 30

Trp Ser Pro Ile Asp Ile His His Leu Ser Cys Pro Asn Asn Leu Val
35 40 45

Val Glu Asp Glu Gly Cys Thr Asn Leu Ser Gly Phe Ser Tyr Met Glu
50 55 60

Leu Lys Val Gly Tyr Ile Ser Ala Ile Lys Met Asn Gly Phe Thr Cys
65 70 75 80

Thr Gly Val Val Thr Glu Ala Glu Thr Tyr Thr Asn Phe Val Gly Tyr
85 90 95

Val Thr Thr Thr Phe Lys Arg Lys His Phe Arg Pro Thr Pro Asp Ala
100 105 110

Cys Arg Ala Ala Tyr Asn Trp Lys Met Ala Gly Asp Pro Arg Tyr Glu
115 120 125

Glu Ser Leu His Asn Pro Tyr Pro Asp Tyr His Trp Leu Arg Thr Val
130 135 140

Lys Thr Thr Lys Glu Ser Leu Val Ile Ile Ser Pro Ser Val Ala Asp
145 150 155 160

Leu Asp Pro Tyr Asp Arg Ser Leu His Ser Arg Val Phe Pro Gly Gly
165 170 175

Asn Cys Ser Gly Val Ala Val Ser Ser Thr Tyr Cys Ser Thr Asn His
180 185 190

Asp Tyr Thr Ile Trp Met Pro Glu Asn Pro Arg Leu Gly Met Ser Cys

```
            195                 200                 205
Asp Ile Phe Thr Asn Ser Arg Gly Lys Arg Ala Ser Lys Gly Ser Glu
210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
            245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
            275                 280                 285

His Leu Val Val Glu Glu Val Lys Lys Arg Glu Glu Cys Leu Asp
290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
370                 375                 380

Gly Pro Asp Gly Asn Val Leu Ile Pro Glu Met Gln Ser Ser Leu Leu
385                 390                 395                 400

Gln Gln His Met Glu Leu Leu Val Ser Ser Val Ile Pro Leu Met His
            405                 410                 415

Pro Leu Ala Asp Pro Ser Thr Val Phe Lys Asn Gly Asp Glu Ala Glu
            420                 425                 430

Asp Phe Val Glu Val His Leu Pro Asp Val His Glu Arg Ile Ser Gly
            435                 440                 445

Val Asp Leu Gly Leu Pro Asn Trp Gly Lys Tyr Val Leu Leu Ser Ala
450                 455                 460

Gly Ala Leu Thr Ala Leu Met Leu Ile Ile Phe Leu Met Thr Cys Trp
465                 470                 475                 480

Arg Arg Val Asn Arg Ser Glu Pro Thr Gln His Asn Leu Arg Gly Thr
            485                 490                 495

Gly Arg Glu Val Ser Val Thr Pro Gln Ser Gly Lys Ile Ile Ser Ser
            500                 505                 510

Trp Glu Ser Tyr Lys Ser Gly Gly Glu Thr Gly Leu
            515                 520

<210> SEQ ID NO 3
<211> LENGTH: 13
<212> TYPE: DNA
<213> ORGANISM: Artificial Sequence
<220> FEATURE:
<223> OTHER INFORMATION: 5' flanking sequence

<400> SEQUENCE: 3
ggcgcgccgc acc                                                          13

<210> SEQ ID NO 4
<211> LENGTH: 1575
<212> TYPE: RNA
<213> ORGANISM: Artificial Sequence
```

-continued

```
<220> FEATURE:
<223> OTHER INFORMATION: codon optimized for humans

<400> SEQUENCE: 4
auggugccgc aggcucuccu guuugucccc cuucuggucu uuccauugug uuuugggaaa        60
uucccuaucu acacaauucc ggacaaguug ggacccugga gcccaauuga cauucaucau       120
cucagcugcc cgaacaauuu ggucguggag gacgaaggau gcaccaaccu gucggguuc        180 uccuacaugg aauugaaagu cggauacauc agugccauua agaugaacgg guucacuugc       240
acaggcgucg ugacugaagc ugagacauac acuaacuucg ugggauaugu cacuaccacu       300
uucaaaagaa agcauuuccg cccuacuccu gaugcuugua gggccgcaua caacuggaag       360
auggccggug accccagaua ugaggaauca cuucacaauc cguacccuga cuaccacugg       420
cuucggacug ucaaaaccac caaggaguca cucgugauca uuaguccaag uguggcugau       480
cuugacccau acgaccgguc acuucacuca cggguguucc cgggggggaa uugcucuggu       540
gucgcagugu cgucaaccua cugcuccaca aaccacgauu acaccauuug gaugccagaa       600
aauccucggc uugguauguc augugacauu uuccaccaauu cucggggaa gagggcuucc       660 aaagggucug aaacuugcgg cuuugucgau gagcggggcu uguauaaguc acuuaaaggu       720
gcuugcaaac ucaagcuuug uggugucuug ggauugagau ugauggaugg aacuuggguc       780
gcaaugcaga cuucuaacga aaccaaaugg ugcccucccg gacagcuugu gaauuugcau       840
gacuuucgcu cugacgaaau ugagcaucuu gucgucgagg aguuggucaa gaagcgggaa       900
gagugucugg augcuuugga aucaaucaug accaccaagu cagugucuuu cagacggcuc       960
ucacaucuua ggaaauuggu gccagguuuu ggaaaagcau auaccauuuu caacaagacc      1020
cuuauggaag ccgaugcuca cuacaagucu gucaggacuu ggaaugagau caucccgucu      1080
aaaggguguc uuaggguucgg agggagaugu cauccucaug ucaacggagu cuuuucaau       1140 gguaucauuc uuggaccuga cggaaaugcc cuuauccug agaugcaauc uucccuccuc       1200
cagcaacaca uggaacuucu ugucucaucg gucaucccc uuaugcaccc ccuggcugac       1260
ccaucaaccg uguucaagaa cgguagacgag gcagaggauu uugucgaggu ccaccuuccc      1320
gaugugcaug aacggaucuc uggugucgac cuuggacucc cuaacugggg aaaguauguc      1380
cuucugucgg caggagcccu gacugccuug auguugauua ucuuccugau gacuuguugg      1440
aggagaguca aucggucgga gccaacacaa cauaaucuca gaggaacagg aagggaggug      1500
ucagucacac cccaaagcgg gaagaucauu ucgucuuggg agucauacaa gagcggaggu      1560
gaaaccggac uguga                                                       1575
```

RABIES VIRUS VACCINE

CROSS-REFERENCE TO RELATED APPLICATIONS

This application is a national stage entry under 35 U.S.C. § 371 of PCT/EP2018/080086, filed on Nov. 5, 2018, which claims priority under 35 U.S.C. § 119(e) of provisional application U.S. Ser. No. 62/581,955 filed Nov. 6, 2017, the contents of which are is hereby incorporated by reference in their entireties.

FIELD OF THE INVENTION

The present invention relates to new vaccines for rabies virus. Methods of making and using the vaccine alone or in combinations with other protective agents are also provided.

BACKGROUND

Rabies is a preventable zoonotic disease that leads to inflammation of the brain in humans and other mammals. Clinical rabies is an acute, progressive encephalitis that is typically classified as either furious or paralytic rabies. Furious rabies is characterized by restlessness, irritability and aggression. Paralytic rabies is characterized by excessive salivation, deep, labored breathing, paralysis and eventually coma.

The causative agent of rabies is the rabies virus, which is capable of infecting most mammals and maintains a reservoir of disease in wild and susceptible domestic animals. The rabies virus is present in most parts of the world, although different species act as the primary reservoir for the rabies virus within various geographical regions, including feral dogs, raccoons, skunks, foxes, bats and mongooses [Robinson et al., *Semin Vet Med Surg* (small Anim) 6:203-211 (1991)]. The rabies virus is most commonly transmitted through the bite of an infected animal. Once the rabies virus infects the central nervous system the clinical signs of rabies manifest.

The rabies virus is an enveloped, RNA virus that encodes five structural proteins: a nucleoprotein (N), a phosphoprotein (P), a matrix protein (M), a glycoprotein (G), and an RNA-dependent RNA polymerase [Dietzschold et al., *Crit Rev Immunol* 10:427-439 (1991)]. The glycoprotein (G) is considered the protective antigen which induces virus neutralizing antibodies [Cox et al., Infect Immun 16:754-759 (1977)]. Several types of rabies vaccines have been produced to combat this disease. Inactivated cell culture derived whole-virus killed rabies virus vaccines are the most commonly used vaccines in the United States. These whole-virus killed rabies virus vaccines require high levels of antigen and therefore, require an adjuvant. Unfortunately, this use of an adjuvant is associated with injection site reactivity, hypersensitivity, and even with the perceived risk of injection site sarcomas in cats. Recently, a modified live vaccine has been used successfully used with oral vaccine baits for the immunization of wild animals [Mahl et al., *Vet Res* 45(1):77 (2014)]. In addition, a recombinant vaccine expressing the glycoprotein (G) is currently being marketed in the United States for use in cats. Nucleic acid vaccines also have been used in laboratory studies, though none are currently licensed in the United States.

A number of vector strategies have been employed in vaccines through the years in an effort to protect against certain animal pathogens. One such vector strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)], which have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health Res Rev.* 13(1):1-9. (2012)]. The RP platform has been used to encode pathogenic antigens and is the basis for several USDA-licensed vaccines for swine and poultry.

Despite the wide availability of whole-virus killed rabies vaccines, as well as the introduction of the newer vaccines, rabies still continues to pose a threat to both domestic animals and humans. Therefore, there remains the long-standing need for new rabies vaccines that will aid in the protection of mammals, including cats, dogs, horses, ferrets, sheep, and cattle, from this debilitating disease.

The citation of any reference herein should not be construed as an admission that such reference is available as "prior art" to the instant application.

SUMMARY OF THE INVENTION

Accordingly, the present invention provides vectors that encode one or more rabies virus antigens. Such vectors can be used in immunogenic compositions comprising these vectors. The immunogenic compositions of the present invention may be used in vaccines. In one aspect of the present invention, a vaccine protects the vaccinated subject (e.g., mammal) against rabies virus. In one embodiment of this type, the vaccinated subject is a canine. In another embodiment, the vaccinated subject is a feline. In a more particular embodiment of this type, the vaccinated subject is a domestic cat. In yet another embodiment, the mammal is an equine (e.g., horse). The present invention further provides combination vaccines for eliciting protective immunity against rabies and other diseases, e.g., other canine, equine, and/or feline infectious diseases. Methods of making and using the immunogenic compositions and vaccines of the present invention are also provided.

In specific embodiments, the vector is an alphavirus RNA replicon particle that encodes one or more antigens that originate from a rabies virus. In even more particular embodiments, the alphavirus RNA replicon particle is a Venezuelan Equine Encephalitis (VEE) alphavirus RNA replicon particle. In still more specific embodiments the VEE alphavirus RNA replicon particle is a TC-83 VEE alphavirus RNA replicon particle. In other embodiments, the alphavirus RNA replicon particle is a Sindbis (SIN) alphavirus RNA replicon particle. In still other embodiments, the alphavirus RNA replicon particle is a Semliki Forest virus (SFV) alphavirus RNA replicon particle. In an alternative embodiment a naked DNA vector comprises a nucleic acid construct that encodes a rabies virus glycoprotein (G) antigen. The present invention includes all of the nucleic acid constructs of the present invention including RNA plasmids, RNA replicons, as well as all of the alphavirus RNA replicon particles of the present invention, the naked DNA vectors, and the immunogenic compositions and/or vaccines that comprise the nucleic acid constructs (e.g., RNA plasmids, RNA replicons) the alphavirus RNA replicon particles, and/or the naked DNA vectors of the present invention.

In certain embodiments the alphavirus RNA replicon particles encode one rabies virus G antigen. In related embodiments, the alphavirus RNA replicon particles encode one or more rabies virus G antigens or antigenic fragments thereof. In still other embodiments, alphavirus RNA replicon particles encode two to four rabies virus G antigens or antigenic fragments thereof. In specific embodiments the alphavirus RNA replicon particles are Venezuelan Equine Encephalitis (VEE) alphavirus RNA replicon particles.

The present invention also provides immunogenic compositions that comprise alphavirus RNA replicon particles that encode one rabies virus G antigen. In related embodiments, the immunogenic compositions comprise alphavirus RNA replicon particles that encode one or more rabies virus G antigens or antigenic fragments thereof. In particular embodiments of this type, the immunogenic compositions comprise alphavirus RNA replicon particles that encode two to four rabies virus G antigens or antigenic fragments thereof. In more particular embodiments, the immunogenic composition comprises alphavirus RNA replicon particles that are Venezuelan Equine Encephalitis (VEE) alphavirus RNA replicon particles.

In other embodiments, the immunogenic composition comprises two or more sets of alphavirus RNA replicon particles. In particular embodiments of this type, one set of alphavirus RNA replicon particles encode the rabies virus G antigen or an antigenic fragment thereof, and the second set of alphavirus RNA replicon particles encode a feline calicivirus (FCV) antigen or an antigenic fragment thereof. In certain embodiments of this type, the FCV antigen originates from a virulent systemic feline calicivirus. In other embodiments the FCV antigen originates from a classic (F9-like) feline calicivirus. In yet other embodiments, the second set of alphavirus RNA replicon particles encode two FCV antigens, one of which originates from a virulent systemic feline calicivirus, whereas the other originates from a classic (F9-like) feline calicivirus.

Accordingly, in certain embodiments a nucleic acid construct of the present invention encodes one or more rabies virus G antigens or antigenic fragments thereof. In particular embodiments of this type, the nucleic acid construct encodes two to four rabies virus G antigens or antigenic fragments thereof. In related embodiments, alphavirus RNA replicon particles comprise a nucleic acid construct that encodes one or more rabies virus G antigens or antigenic fragments thereof. In still other embodiments, alphavirus RNA replicon particles comprise a nucleic acid construct that encodes two to four rabies virus G antigens or antigenic fragments thereof.

In particular embodiments, immunogenic compositions comprise alphavirus RNA replicon particles that comprise a nucleic acid construct that encodes one or more rabies virus G antigens or antigenic fragments thereof. In related embodiments, the immunogenic compositions comprise alphavirus RNA replicon particles that encodes two to four rabies virus G antigens or antigenic fragments thereof. In particular embodiments of this type, the alphavirus RNA replicon particles encode rabies virus G or an antigenic fragment thereof. In more particular embodiments, the immunogenic composition comprises alphavirus RNA replicon particles that are Venezuelan Equine Encephalitis (VEE) alphavirus RNA replicon particles. In other embodiments, the immunogenic composition comprises two or more sets of alphavirus RNA replicon particles. In particular embodiments of this type, one set of alphavirus RNA replicon particles comprises a first nucleic acid construct, whereas the other set of alphavirus RNA replicon particles comprise a second nucleic acid construct.

In yet other embodiments, the immunogenic composition comprises one set of alphavirus RNA replicon particles that comprise a first nucleic acid construct, another set of alphavirus RNA replicon particles that comprise a second nucleic acid construct, and a third set of alphavirus RNA replicon particles that comprise a third nucleic acid construct. In a particular embodiment of this type, the first nucleic acid construct encodes a rabies virus G antigen or an antigenic fragment thereof, the second nucleic acid construct encodes a feline calicivirus (FCV) antigen which originates from a virulent systemic feline calicivirus or an antigenic fragment thereof, and the third nucleic acid construct encodes a feline calicivirus (FCV) antigen which originates from a classic (F9-like) feline calicivirus or an antigenic fragment thereof. In particular embodiments, the feline calicivirus (FCV) antigen is the FCV capsid protein.

In still other embodiments, the immunogenic composition comprises a set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, a fourth set of alphavirus RNA replicon particles that comprise a fourth nucleic acid construct, and a fifth set of alphavirus RNA replicon particles that comprise a fifth nucleic acid construct. In such embodiments, the nucleotide sequences of the first nucleic acid construct, the second nucleic acid construct, third nucleic acid construct, the fourth nucleic acid construct, and the fifth nucleic acid construct are all different.

Accordingly, an immunogenic composition of the present invention can contain alphavirus RNA replicon particles that comprise a nucleic acid construct that, in addition, encodes at least one non-rabies virus antigen for eliciting protective immunity to a non-rabies virus pathogen. In particular embodiments of this type, the non-rabies virus antigen is a protein antigen that originates from feline herpesvirus (FHV). In other embodiments, the non-rabies virus antigen is a protein antigen that originates from feline calicivirus (FCV). In yet other embodiments, the non-rabies virus antigen is a protein antigen that originates from feline pneumovirus (FPN). In still other embodiments, the non-rabies virus antigen is a protein antigen that originates from feline parvovirus (FPV).

In still other embodiments, the immunogenic composition comprises one set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, and a fourth set of alphavirus RNA replicon particles that comprise a fourth nucleic acid construct. In a particular embodiment of this type, the first nucleic acid construct encodes a rabies virus G antigen or an antigenic fragment thereof, the second nucleic acid construct encodes a feline calicivirus (FCV) antigen which originates from a virulent systemic feline calicivirus or an antigenic fragment thereof, the third nucleic acid construct encodes a feline calicivirus (FCV) antigen which originates from a classic (F9-like) feline calicivirus or an antigenic fragment thereof, and the fourth nucleic acid construct encodes a FeLV antigen or an antigenic fragment thereof.

In yet other embodiments, the immunogenic composition comprises a set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, a fourth set of alphavirus RNA replicon particles that comprise a fourth nucleic acid construct, and a fifth set of alphavirus RNA replicon particles that comprise a fifth nucleic acid construct. In such embodiments, the nucleotide sequences of the first nucleic acid construct, the second nucleic acid construct, third nucleic acid construct, the fourth nucleic acid construct, and the fifth nucleic acid construct are all different.

Accordingly, an immunogenic composition of the present invention can contain alphavirus RNA replicon particles that comprise a nucleic acid construct that encodes at least one non-rabies virus antigen for eliciting protective immunity to a non-rabies virus pathogen. In particular embodiments of this type, the non-rabies virus antigen is a protein antigen that originates from feline herpesvirus (FHV). In other embodiments, the non-rabies virus antigen is a protein antigen that originates from feline calicivirus (FCV). In yet other embodiments, the non-rabies virus antigen is a protein antigen that originates from feline pneumovirus (FPN). In still other embodiments, the non-rabies virus antigen is a protein antigen that originates from feline parvovirus (FPV).

The present invention further provides combination immunogenic compositions and/or vaccines that include alphavirus RNA replicon particles that encode an antigen or antigenic fragment thereof originating from rabies virus together with one or more modified live (e.g., attenuated) or killed mammalian pathogens.

In particular embodiments of the present invention, the rabies virus antigen is the rabies virus G. In specific embodiments of this type the rabies virus G comprises an amino acid sequence comprising 95% identity or more with the amino acid sequence of SEQ ID NO: 2. In more specific embodiments of this type the rabies virus G comprises the amino acid sequence of SEQ ID NO: 2. In even more specific embodiments of this type the rabies virus G is encoded by the nucleotide sequence of SEQ ID NO: 1 or SEQ ID NO: 4.

The present invention further comprises vaccines and multivalent vaccines comprising the immunogenic compositions of the present invention. In particular embodiments, the vaccines are nonadjuvanted vaccine. The vaccines of the present invention can aid in the prevention of disease associated with rabies virus. In certain embodiments, antibodies are induced in a mammalian subject when the mammal is immunized with the vaccine. In particular embodiments, the mammal is a canine. In other embodiments, the mammal is a feline. In yet other embodiments, the mammal is an equine (horse). In still other embodiments, the mammal is a mustelid. In particular embodiments of this type, the mustelid is a ferret. In yet other embodiments, the mammal is a bovidae. In particular embodiments of this type, the bovidae is a bovine. In other embodiments of this type, the bovidae is a sheep.

The present invention also provides methods of immunizing a mammal against rabies virus comprising administering to the mammal an immunologically effective amount of a vaccine of the present invention. In particular embodiments the vaccine is administered via intramuscular injection. In alternative embodiments the vaccine is administered via subcutaneous injection. In other embodiments the vaccine is administered via intravenous injection. In still other embodiments the vaccine is administered via intradermal injection. In yet other embodiments the vaccine is administered via oral administration. In still other embodiments the vaccine is administered via intranasal administration. In specific embodiments, the mammal is a cat. In other specific embodiments, the mammal is a canine. In still other embodiments, the mammal is a horse.

The vaccines (including multivalent vaccines) of the present invention can be administered as a primer vaccine and/or as a booster vaccine. In specific embodiments, a vaccine of the present invention is administered as a one shot vaccine (one dose), without requiring subsequent administrations. In the case of the administration of both a primer vaccine and a booster vaccine in certain embodiments, the primer vaccine and the booster vaccine can be administered by the identical route. In other embodiments of this type, the primer vaccine and the booster vaccine are both administered by subcutaneous injection. In alternative embodiments, the administration of the primer vaccine can be performed by one route and the booster vaccine by another route. In certain embodiments of this type, the primer vaccine can be administered by subcutaneous injection and the booster vaccine can be administered orally.

The invention further provides methods of immunizing a mammal against rabies virus comprising injecting the mammal with an immunologically effective amount of a vaccine of the invention. In particular embodiments, the vaccine can include from about $1\times10^5$ to about $1\times10^{10}$ RPs or higher. In more particular embodiments, the vaccines can include from about $1\times10^6$ to about $1\times10^9$ RPs. In even more particular embodiments, the vaccines can include from about $1\times10^7$ to about $1\times10^8$ RPs.

In certain embodiments, the vaccines of the present invention are administered in 0.03 mL to 5 mL doses. In particular embodiments, the vaccines of the present invention are administered in 0.05 mL to 3 mL doses. In more particular embodiments, the dose administered is 0.1 mL to 2 mLs. In still more particular embodiments, the dose administered is 0.2 mL to 1.5 mLs. In even more particular embodiments, the dose administered is 0.3 to 1.0 mLs. In still more particular embodiments, the dose administered is 0.4 mL to 0.8 mLs.

These and other aspects of the present invention will be better appreciated by reference to the following Detailed Description.

DETAILED DESCRIPTION OF THE INVENTION

The present invention provides vaccine compositions that include an immunologically effective amount of an antigen from one or more strains of rabies virus that aids in eliciting protective immunity in the recipient vaccinated animal. In one aspect of the present invention, the vaccines comprise alphavirus RNA replicon particles (RPs) that comprise the capsid protein and glycoproteins of Venezuelan Equine Encephalitis Virus (VEE) and encode the rabies glycoprotein (G) or an antigenic fragment thereof. In even more specific embodiments, the vaccines comprise alphavirus RNA replicon particles (RPs) that comprise the capsid protein and glycoproteins of the avirulent TC-83 strain of VEE and encode the rabies glycoprotein (G) or an antigenic fragment thereof. In another aspect of the present invention, the vaccines comprise naked DNA vectors that encode the rabies glycoprotein (G). Vaccines comprising the alphavirus RNA replicon particles encoding rabies glycoprotein (G) can be administered in the absence of an adjuvant and still effectively aid in eliciting protective immunity in the vaccinated mammal against rabies virus.

Accordingly, one aspect of the invention provides an improved, safe nonadjuvanted rabies virus vaccine. In a related aspect, the vaccines of the present invention do not induce injection-site sarcomas, yet still provide protection to the vaccinated mammal from the debilitating disease state caused by a rabies virus infection, that are at least as efficacious as the corresponding adjuvanted vaccines.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1 \times 10^8$ alphavirus RNA replicon particles per milliliter contains from $5 \times 10^7$ to $1.5 \times 10^8$ alphavirus RNA replicon particles per milliliter.

As used herein, the term "feline" refers to any member of the Felidae family. Domestic cats, pure-bred and/or mongrel companion cats, and wild or feral cats are all felines.

As used herein the term, "canine" includes all domestic dogs, *Canis lupus familiaris* or *Canis familiaris*, unless otherwise indicated.

As used herein, a "ferret" is a mammal that is one of the mammals that belong to the mustelid family.

As used herein, a "bovidae" is a mammalian family of cloven-hoofed, ruminant mammals that includes antelopes, sheep (ovine), goats, muskoxen, and bovine, e.g., bison, African buffalo, water buffalo, and cattle.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [*Virology* 239(2):389-401 (1997)]. An RP cannot propagate in cell cultures or animal hosts (without a helper plasmid or analogous component), because the replicon does not encode the alphavirus structural components (e.g., capsid and glycoproteins).

The term "non-rabies virus", is used to modify terms such as pathogen, and/or antigen (or immunogen) to signify that the respective pathogen, and/or antigen (or immunogen) is neither a rabies virus nor a rabies virus antigen (or immunogen) and that a non-rabies virus protein antigen (or immunogen) does not originate from a rabies virus.

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence, within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "protecting", or "providing protection to", or "eliciting protective immunity to", or "aids in the prevention of a disease" and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., a canine (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates.

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., a canine.

Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity.

These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

For the purposes of this invention, an "inactivated" microorganism is an organism which is capable of eliciting an immune response in an animal, but is not capable of infecting the animal. For example, an inactivated rabies virus may be inactivated by an agent selected from the group consisting of binary ethyleneimine, formalin, beta-propiolactone, thimerosal, or heat.

The alphavirus RNA replicon particles of the present invention may be lyophilized and rehydrated with a sterile water diluent. On the other hand, when the alphavirus RNA replicon particles are stored separately, but intend to be mixed with other vaccine components prior to administration, the alphavirus RNA replicon particles can be stored in the stabilizing solution of those components, e.g., a high sucrose solution.

A vaccine of the present invention can be readily administered by any standard route including intravenous, intramuscular, subcutaneous, oral, intranasal, intradermal, and/or intraperitoneal vaccination. The artisan will appreciate that the vaccine composition is preferably formulated appropriately for each type of recipient animal and route of administration. Thus, the present invention also provides methods of immunizing a mammal against rabies and/or other mammalian pathogens. One such method comprises injecting a mammal with an immunologically effective amount of a vaccine of the present invention, so that the mammal produces appropriate rabies virus glycoprotein (G) antibodies.

Multivalent Vaccines:

The present invention also provides multivalent vaccines. Any antigen or combination of such antigens useful in a mammalian vaccine can be added to a propagation defective alphavirus RNA replicon particle (RP) that encodes a mammalian antigen of the rabies virus [e.g., the rabies glycoprotein (G)] in the vaccine. Accordingly, such multivalent vaccines are included in the present invention.

SEQUENCE TABLE

| SEQ ID NO: | Description | Type |
|---|---|---|
| 1 | Rabies Glycoprotein | nucleic acid (DNA) |
| 2 | Rabies Glycoprotein | amino acid |
| 3 | GGCGCGCCGCACC | nucleic acid |
| 4 | Rabies Glycoprotein | nucleic acid (RNA) |
|  | TTAATTAA | nucleic acid |

Sequences

The Rabies glycoprotein (G) gene was codon-optimized for humans. The resulting gene has only ~85% nucleotide identity to live rabies virus glycoprotein (G) sequence, despite having 100% amino acid identity.

RABIES VIRUS G (SEQ ID NO: 1)

atggtgccgcaggctctcctgtttgtccccttctggtctttccattgtg ttttgggaaattccctatctacacaattccggacaagttgggaccctgga gcccaattgacattcatcatctcagctgcccgaacaatttggtcgtggag gacgaaggatgcaccaacctgtcggggttctcctacatggaattgaaagt cggatacatcagtgccattaagatgaacgggttcacttgcacaggcgtcg tgactgaagctgagacatacactaacttcgtgggatatgtcactaccact ttcaaaagaaagcatttccgccctactcctgatgcttgtagggccgcata caactggaagatggccggtgacccagatatgaggaatcacttcacaatc cgtaccctgactaccactggcttcggactgtcaaaaccaccaaggagtca ctcgtgatcattagtccaagtgtggctgatcttgacccatacgaccggtc acttcactcacgggtgttcccggggggaattgctctggtgtcgcagtgt cgtcaacctactgctccacaaaccacgattacaccatttggatgccagaa aatcctcggcttggtatgtcatgtgacattttcaccaattctcggggaa gagggcttccaaagggtctgaaacttgcggctttgtcgatgagcgggct tgtataagtcacttaaaggtgcttgcaaactcaagctttgtggtgtcttg ggattgagattgatggatggaacttgggtcgcaatgcagacttctaacga aaccaaatggtgccctcccggacagcttgtgaatttgcatgactttcgct ctgacgaaattgagcatcttgtcgtcgaggagttggtcaagaagcgggaa gagtgtctggatgctttggaatcaatcatgaccaccaagtcagtgtcttt

```
cagacggctctcacatcttaggaaattggtgccaggttttggaaaagcat ataccattttcaacaagacccttatggaagccgatgctcactacaagtct gtcaggacttggaatgagatcatcccgtctaaagggtgtcttagggtcgg agggagatgtcatcctcatgtcaacggagtctttttcaatggtatcattc ttggacctgacggaaatgtccttatccctgagatgcaatcttccctcctc cagcaacacatggaacttcttgtctcatcggtcatccccttatgcaccc cctggctgacccatcaaccgtgttcaagaacggtgacgaggcagaggatt ttgtcgaggtccaccttcccgatgtgcatgaacggatctctggtgtcgac cttggactccctaactggggaaagtatgtccttctgtcggcaggagccct gactgccttgatgttgattatcttcctgatgacttgttggaggagagtca atcggtcggagccaacacaacataatctcagaggaacaggaagggaggtg tcagtcacaccccaaagcgggaagatcatttcgtcttgggagtcatacaa gagcggaggtgaaaccggactgtga
```

RABIES VIRUS G (SEQ ID NO: 2)
MVPQALLFVPLLVFPLCFGKFPIYTIPDKLGPWSPIDIHHLSCPNNLVVE

DEGCTNLSGFSYMELKVGYISAIKMNGFTCTGVVTEAETYTNFVGYVTTT

FKRKHFRPTPDACRAAYNWKMAGDPRYEESLHNPYPDYHWLRTVKTTKES

LVIISPSVADLDPYDRSLHSRVFPGGNCSGVAVSSTYCSTNHDYTIWMPE

NPRLGMSCDIFTNSRGKRASKGSETCGFVDERGLYKSLKGACKLKLCGVL

GLRLMDGTWVAMQTSNETKWCPPGQLVNLHDFRSDEIEHLVVEELVKKRE

ECLDALESIMTTKSVSFRRLSHLRKLVPGFGKAYTIFNKTLMEADAHYKS

VRTWNEIIPSKGCLRVGGRCHPHVNGVFFNGIILGPDGNVLIPEMQSSLL

QQHMELLVSSVIPLMHPLADPSTVFKNGDEAEDFVEVHLPDVHERISGVD

LGLPNWGKYVLLSAGALTALMLIIFLMTCWRRVNRSEPTQHNLRGTGREV

SVTPQSGKIISSWESYKSGGETGL*

RABIES VIRUS G (SEQ ID NO: 4)
```
auggugccgcaggcucuccuguuugucccccuucggucuuuccauugug uuuugggaaauucccuaucuacacaauuccggacaaguugggacccugga gcccaauugacauucaucaucucagcugcccgaacaauuuggucguggag gacgaaggaugcaccaaccgucggggguucuccuacauggaaugaaagu cggauacaucagugccauuaagaugaacggguucacuugcacaggcgucg ugacugaagcugagacauacacuaacuucgugggauaugucacuaccacu uucaaaagaaagcauuccgcccuacuccugaugcuguagggccgcaua caacuggaagauggccggugaccccagauagagaacaccuucacaauc cguacccugacuaccacuggcuucggacugucaaaaccaccaaggaguca cucgugaucauuaguccaagugugugcugaucuugacccauacgaccgguc acuucacucacggguguucccgggggggaauugcucgguugucgcagugu cgucaaccuacugcuccacaaaccacgauuacaccauuggaugccagaa aauccucggcuugguaugucauguagacauuucaccaauucucgggggaa gagggcuuccaaagggucugaaacuugcggcuuugucgaugagcgggcu uguauaagucacuuaaaggugcuugcaaacucaagcuuugugugucuug
``` ggauugagauugauggauggaacuugggucgcaaugcagacuucuaacga aaccaaauggugcccucccggacagcuugugaauuugcaugacuuucgcu cugacgaaauugagcaucuugucgucgaggaguuggucaagaagcgggaa gagugucuggaugcuuuggaaucaaucaugaccaccaagucagugucuuu cagacggcucucacaucuuaggaaauuggugccagguuuuggaaaagcau auaccauuuucaacaagacccuuauggaagccgaugcucacuacaagucu gucaggacuuggaaugagaucaucccgucuaaagggugucuuagggucgg agggagaugucauccucaugucaacggagucuuuuucaaugguaucauuc uuggaccugacggaaaugucucuuauccugaugcaaucuuccccuccuc cagcaacacauggaacuucuugcucaucggucauccccuuaugcaccc ccuggcugacccaucaaccguguucaagaacggugacgaggcagaggauu uugucgagguccaccuucccgaugugcaugaacggaucucuggugucgac cuuggacucccuaacuggggaaaguaugucuucugucggcaggagcccu gacugccuugauguugauuaucuuccugaugacuuguuggaggagaguca aucggucggagccaacacaacauaaucucagaggaacaggaagggaggug ucagucacaccccaaagcgggaagaucauuucgucuugggagucauacaa gagcggaggugaaaccggacuguga

EXAMPLES

The following examples serve to provide further appreciation of the invention, but are not meant in any way to restrict the effective scope of the invention.

Example 1

Incorporation of the Coding Sequences for Rabies Virus Glycoprotein into the Alphavirus RNA Replicon Particles Introduction RNA viruses can be used as vector-vehicles for introducing vaccine antigens that have been genetically engineered into their genomes. However, their use to date has been limited primarily to incorporating viral antigens into the RNA virus and then introducing the virus into a recipient host. The result is the induction of protective antibodies against the incorporated viral antigens. Alphavirus RNA replicon particles have been used to encode pathogenic antigens. Such alphavirus replicon platforms have been developed from several different alphaviruses, including Venezuelan equine encephalitis virus (VEE) [Pushko et al., Virology 239:389-401 (1997)], Sindbis (SIN) [Bredenbeek et al., *Journal of Virology* 67:6439-6446 (1993) the contents of which are hereby incorporated herein in their entireties], and Semliki Forest virus (SFV) [Liljestrom and Garoff, *Biotechnology* (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 19O5.D0), and Prescription Product, RNA Particle (Product Code 9PP0.00).

Alphavirus RNA Replicon Construction

A vaccine was prepared comprising an alphavirus RNA replicon particle encoding the rabies virus glycoprotein (G) from rabies virus packaged with the capsid protein and glycoproteins of the avirulent TC-83 strain of Venezuelan Equine Encephalitis Virus. The nucleotide sequence for the rabies virus G protein was codon-optimized for humans. The resulting sequence has only ~85% nucleotide identity to a live rabies virus glycoprotein (G) sequence, despite having 100% amino acid identity. The vaccine can be used as a single dose administered to a mammalian subject, e.g., subcutaneously to cats and dogs aged 12 weeks or older or alternatively, in a multiple dose comprising a primary administration followed by one or more booster administrations.

An amino acid sequence for Rabies virus glycoprotein (G) was used to generate codon-optimized (human codon usage) nucleotide sequences in silico. Optimized sequences were prepared as synthetic DNA by a commercial vendor (ATUM, Newark, CA). Accordingly, a synthetic gene [SEQ ID NO: 1] was designed based on the amino acid sequence of Rabies virus Glycoprotein. The construct (RABV-G) was a wild-type amino acid sequence [SEQ ID NO: 2], codon-optimized for humans, with flanking sequence appropriate for cloning into the alphavirus replicon plasmid.

The VEE replicon vectors that were designed to express Rabies virus G were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes Ascl and Pacl. A DNA plasmid containing the codon-optimized open reading frame nucleotide sequence of the Rabies G gene, with 5' flanking sequence (5'-GGCGCGCCGCACC-3') [SEQ ID NO: 3] and 3' flanking sequence (5'-TTAATTAA-3') was similarly digested with restriction enzymes Ascl and Pacl. The synthetic gene cassette was then ligated into the digested pVEK vector, and the resulting clone was re-named "pVHV-RABV-G". The "pVHV" vector nomenclature was chosen to refer to pVEK-derived replicon vectors containing transgene cassettes cloned via the Ascl and Pacl sites in the multiple cloning site of pVEK.

Production of TC-83 RNA replicon particles (RP) was conducted according to methods previously described [U.S. Pat. Nos. 9,441,247 B2 and 8,460,913 B2; the contents of which are hereby incorporated herein by reference]. Briefly, pVHV replicon vector DNA and helper DNA plasmids were linearized with NotI restriction enzyme prior to in vitro transcription using MegaScript T7 RNA polymerase and cap analog (Promega, Madison, WI). Importantly, the helper RNAs used in the production lack the VEE subgenomic promoter sequence, as previously described [Kamrud et al., J Gen Virol. 91(Pt 7):1723-1727 (2010)]. Purified RNA for the replicon and helper components were combined and mixed with a suspension of Vero cells, electroporated in 4 mm cuvettes, and returned to OptiPro® SFM cell culture media (Thermo Fisher, Waltham, MA). Following overnight incubation, alphavirus RNA replicon particles were purified from the cells and media by passing the suspension through a ZetaPlus BioCap® depth filter (3M, Maplewood, MN), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. The titer of functional RP was determined with an immunofluorescence assay on infected Vero cell monolayers.

Example 2

Vaccines Containing Alphavirus RNA Replicon Particles Encoding Rabies Virus Glycoprotein Administered to Canines An initial study was conducted to evaluate the safety and serological response in dogs following vaccination with the RP-rabies virus G vaccine. The RP-rabies virus G vaccines for the study were formulated in 5% sucrose and 1% canine serum as stabilizer and the liquid vaccine is frozen for storage. Five groups of five dogs each were vaccinated as summarized below:

TABLE 1

ADMINISTRATION OF THE RP-RABIES VIRUS G VACCINE TO CANINES

| Group | No. of Animals | Vaccine | RP/dose | Vaccination Days |
|---|---|---|---|---|
| 1 | 5 | RP-Rabies | $4.1 \times 10^8$ | 0 |
| 2 | 5 | RP-Rabies | $5.0 \times 10^7$ | 0 |
| 3 | 5 | RP-Rabies | $8.3 \times 10^6$ | 0 |
| 4 | 5 | Commercial # | | 0 |
| 5 | 5 | Placebo* | $3.9 \times 10^7$ | 0, 21 |

The commercial vaccine was DEFENSOR ® 3 (sold by Zoetis).
*The placebo vaccine was an RP encoding a canine non-rabies virus insert (RP-NR), rather than a rabies virus antigen.

Dogs, 12-13 weeks of age, were vaccinated with 1.0 mL of the respective vaccine (see, Table 1 above), administered subcutaneously in the right scapular region. As indicated, the dogs in Group four received a currently licensed, commercial rabies vaccine DEFENSOR® 3, which is sold by Zoetis. The dogs in Group five received an unrelated RP construct, a canine non-rabies virus insert (RP-NR), as the placebo. Following vaccination the dogs were observed for adverse reactions to the vaccines by performing a clinical assessment and palpating the injection site 4-8 hours after vaccination and daily for seven days post-vaccination. No adverse local or systemic reactions to any of the vaccines was observed. The dogs were bled for serum on the day before vaccination and at one month intervals after vaccination for the first three months of the study. The serum was tested for antibody titer to rabies virus by the Rapid Fluorescent Foci Inhibition Test (RFFIT).

The anti-rabies serology results are presented in Table 2 below. Titers are expressed as International Units per mL (IU/mL), with 0.5 IU/mL regarded as a protective titer.

TABLE 2

SEROLOGY RESULTS FOR A 3 MONTH PERIOD FOLLOWING THE ADMINISTRATION OF THE VACCINE TO CANINES

| Dog ID | Group | Day −1 | Day 30 | Day 59 | Day 90 |
|---|---|---|---|---|---|
| 64914 | 1 | <0.1 | 37.0 | 8.9 | 4.0 |
| 65822 | 1 | 0.2 | 33.0 | 10.0 | 4.0 |
| 66313 | 1 | 0.1 | 38.0 | 11.1 | 4.7 |
| 66356 | 1 | <0.1 | 33.0 | 11.1 | 3.3 |
| 67743 | 1 | <0.1 | 18.5 | 6.6 | 3.3 |
| 64052 | 2 | <0.1 | 12.5 | 2.6 | 2.8 |

TABLE 2-continued

SEROLOGY RESULTS FOR A 3 MONTH PERIOD FOLLOWING
THE ADMINISTRATION OF THE VACCINE TO CANINES

| Dog ID | Group | Day −1 | Day 30 | Day 59 | Day 90 |
|---|---|---|---|---|---|
| 66062 | 2 | <0.1 | 8.5 | 3.1 | 2.2 |
| 67034 | 2 | <0.1 | 17.5 | 3.8 | 2.4 |
| 67085 | 2 | <0.1 | 14.5 | 11.1 | 2.4 |
| 68022 | 2 | 0.1 | 11.0 | 2.8 | 1.3 |
| 63586 | 3 | <0.1 | 13.7 | 3.8 | 2.2 |
| 65864 | 3 | 0.2 | 3.5 | 1.1 | 0.7 |
| 66593 | 3 | <0.1 | 4.3 | 2.0 | 1.3 |
| 67379 | 3 | <0.1 | 4.7 | 1.3 | 2.0 |
| 67816 | 3 | <0.1 | 13.7 | 1.2 | 0.9 |
| 64451 | 4 | <0.1 | 6.6 | 1.1 | 0.5 |
| 66097 | 4 | <0.1 | 0.2 | <0.1 | <0.1 |
| 66292 | 4 | <0.1 | 2.2 | 0.4 | 0.1 |
| 67620 | 4 | <0.1 | 3.4 | 0.7 | 0.1 |
| 67867 | 4 | <0.1 | 3.4 | 0.6 | 0.1 |
| 62032 | 5 | <0.1 | <0.1 | <0.1 | <0.1 |
| 66003 | 5 | <0.1 | <0.1 | <0.1 | <0.1 |
| 66984 | 5 | <0.1 | <0.1 | <0.1 | <0.1 |
| 67051 | 5 | <0.1 | 0.1 | <0.1 | <0.1 |
| 67701 | 5 | <0.1 | 0.1 | <0.1 | <0.1 |

Though the study was originally intended to end three months after vaccination, the study was extended because the serological titers in the RP-rabies virus groups surprisingly both: (i) remained at protective levels for this time period and (ii) were superior to a currently licensed, commercial rabies vaccine. Five dogs from Group 1, three dogs from Group 2, and two dogs from Group 4 were retained. The remaining dogs were bled for serum at approximately one month intervals for the one year post-vaccination study.

The anti-rabies virus serology results for the first year of the selected dogs are presented in the Table 3 below. The titers are expressed as International Units per mL (IU/mL), with 0.5 IU/mL regarded as a protective titer:

TABLE 3

SEROLOGY RESULTS FOR A 1-YEAR PERIOD FOLLOWING
THE ADMINISTRATION OF THE VACCINE TO CANINES

| Dog ID | Group | Day −1 | Day 30 | Day 59 | Day 90 | Day 120 | Day 150 | Day 181 | Day 210 | Day 240 | Day 300 | Day 330 | Day 365 |
|---|---|---|---|---|---|---|---|---|---|---|---|---|---|
| 64914 | 1 | <0.1 | 37.0 | 8.9 | 4.0 | 2.0 | 0.9 | 1.3 | 0.6 | 2.2 | 0.6 | 0.6 | 0.5 |
| 65822 | 1 | 0.2 | 33.0 | 10.0 | 4.0 | 3.8 | 2.8 | 2.3 | 1.6 | 2.7 | 2.0 | 2.2 | 2.6 |
| 66313 | 1 | 0.1 | 38.0 | 11.1 | 4.7 | 5.9 | 9.0 | 10.6 | 11.1 | 11.8 | 16.0 | 10.8 | 11.0 |
| 66356 | 1 | <0.1 | 33.0 | 11.1 | 3.3 | 3.4 | 3.1 | 1.9 | 2.3 | 2.3 | 1.6 | 2.3 | 2.2 |
| 67743 | 1 | <0.1 | 18.5 | 6.6 | 3.3 | 3.4 | 1.6 | 0.5 | 0.5 | 0.8 | 0.5 | 0.3 | 0.5 |
| 64052 | 2 | <0.1 | 12.5 | 2.6 | 2.8 | 3.1 | 3.0 | 2.1 | 1.6 | 2.5 | 0.8 | 0.7 | 2.0 |
| 66062 | 2 | <0.1 | 8.5 | 3.1 | 2.2 | 1.8 | 2.7 | 1.3 | 1.1 | 1.1 | 1.0 | 0.6 | 1.5 |
| 68022 | 2 | 0.1 | 11.0 | 2.8 | 1.3 | 0.7 | 0.6 | 0.1 | 0.1 | 0.1 | <0.1 | <0.1 | <0.1 |
| 64451 | 4 | <0.1 | 6.6 | 1.1 | 0.5 | 0.1 | 0.1 | 0.1 | 0.1 | 0.2 | <0.1 | <0.1 | 0.1 |
| 67620 | 4 | <0.1 | 3.4 | 0.7 | 0.1 | <0.1 | 0.1 | <0.1 | <0.1 | 0.1 | <0.1 | ≤0.1 | <0.1 |

This initial study was followed up with a second study (currently on-going) that has resulted in analogous results, at least over the six month time period that has transpired.

Example 3

Vaccines Containing Alphavirus RNA Replicon Particles Encoding Rabies Virus Glycoprotein Administered to Felines An initial study was conducted to evaluate the safety and serological response in cats following vaccination with the RP-rabies virus G vaccine. The RP-rabies virus G vaccines for this study were formulated in an experimental liquid stabilizer [see e.g., U.S. Pat. No. 9,314,519 B2] and stored refrigerated at 2-7° C. Four groups of cats were vaccinated as summarized in Table 4 below:

TABLE 4

ADMINISTRATION OF THE RP-RABIES
VIRUS G VACCINE TO FELINES

| Group | No. of Animals | Vaccine | RP/dose |
|---|---|---|---|
| 1 | 10 | RP-Rabies | $2.7 \times 10^7$ |
| 2 | 10 | RP-Rabies | $2.6 \times 10^6$ |
| 3 | 10 | RP-Rabies | $4.0 \times 10^5$ |
| 4 | 5 | Commercial [#] | |

[#] The commercial vaccine was DEFENSOR® 3 (sold by Zoetis).

Cats, 15-16 weeks of age, were vaccinated with 1.0 mL of the respective vaccine (see, Table 4 above), administered subcutaneously in the right scapular region. As indicated, the cats in Group four received a currently licensed, commercial rabies vaccine DEFENSOR® 3, sold by Zoetis, which contains a chemically inactivated rabies virus together with an aluminum hydroxide adjuvant.

Following vaccination the cats were observed for adverse reactions to the vaccines by performing a clinical assessment and palpating the injection site 4-8 hours after vaccination and daily for seven days post-vaccination. Cats were also observed for a period of 10-15 minutes immediately following vaccination for systemic reactions. Some immediate, systemic reactions were observed in cats in Groups 1, 2 and 3, indicating the cats were experiencing a stinging or painful reaction upon injection. These reactions persisted no more than five minutes. These injection reactions were attributed to the composition of the experimental liquid stable formulation. No adverse local reactions were observed after vaccination. The cats were bled for serum on the day before vaccination and at one month intervals after vaccination for the first three months of the study. The serum was tested for antibody titer to rabies virus by the Rapid Fluorescent Foci Inhibition Test (RFFIT). The anti-rabies virus serology results are presented in Table 5 below. Titers are expressed as International Units per mL (IU/mL), with 0.5 IU/mL being regarded as a protective titer.

TABLE 5

SEROLOGY RESULTS FOR A 5-MONTH PERIOD FOLLOWING THE ADMINISTRATION OF THE VACCINE TO FELINES

| ANIMAL ID | Group | Day −1 | Day 30 | Day 58 | Day 91 | Day 120 | Day 149 |
|---|---|---|---|---|---|---|---|
| 16CNH2 | 1 | <0.1 | 119.0 | 69.0 | 40.0 | 37.0 | 106.0 |
| 16CNL4 | | <0.1 | 30.0 | 24.0 | 16.0 | 12.5 | 11.0 |
| 16CNM6 | | <0.1 | 37.0 | 28.0 | 32.0 | 29.0 | 71.0 |
| 16JNA2 | | <0.1 | 19.0 | 30.0 | 27.0 | 22.0 | 23.0 |
| 16JNE1 | | <0.1 | 45.0 | 31.0 | 28.0 | 15.0 | 23.0 |
| 16JNF1 | | <0.1 | 113.0 | 40.0 | 31.0 | 27.0 | 34.0 |
| 16JNG3 | | <0.1 | 45.0 | 31.0 | 16.0 | 12.5 | 26.0 |
| 16JNI1 | | <0.1 | 26.0 | 25.0 | 28.0 | 10.0 | 22.0 |
| 16JNM1 | | <0.1 | 27.0 | 30.0 | 31.0 | 27.0 | 30.0 |
| 16JNM2 | | <0.1 | 50.0 | 28.0 | 32.0 | 26.0 | 26.0 |
| Geometric Mean Titer | | <0.1 | 42.7 | 32.0 | 27.1 | 20.0 | 30.4 |
| 16CMX5 | 2 | <0.1 | 25.0 | 28.0 | 32.0 | 33.0 | 106.0 |
| 16CNF4 | | <0.1 | 10.0 | 9.0 | 5.0 | 5.5 | 5.1 |
| 16CNH4 | | <0.1 | 24.0 | 14.8 | 6.0 | 10.8 | 17.0 |
| 16CNJ2 | | <0.1 | 32.0 | 31.0 | 27.0 | 22.0 | 27.0 |
| 16JNB3 | | <0.1 | 25.0 | 31.0 | 31.0 | 18.0 | 23.0 |
| 16JNB4 | | <0.1 | 23.0 | 30.0 | 31.0 | 23.0 | 26.0 |
| 16JNG2 | | <0.1 | 10.5 | 12.6 | 11.0 | 13.5 | 21.0 |
| 16JNJ1 | | <0.1 | 11.0 | 22.0 | 25.0 | 6.0 | 23.0 |
| 16JNJ2 | | <0.1 | 23.0 | 28.0 | 28.0 | 18.0 | 23.0 |
| 16JNK1 | | <0.1 | 10.0 | 13.4 | 7.0 | 8.3 | 5.0 |
| Geometric Mean Titer | | <0.1 | 17.6 | 20.2 | 16.3 | 13.6 | 19.6 |
| 16CMV3 | 3 | <0.1 | 6.0 | 6.0 | 6.0 | 12.3 | 9.4 |
| 16CNB4 | | <0.1 | 25.0 | 28.0 | 25.0 | 16.0 | 24.0 |
| 16CNB5 | | <0.1 | 33.0 | 36.0 | 40.0 | 27.0 | 38.0 |
| 16CNC5 | | <0.1 | 25.0 | 22.0 | 8.0 | 13.5 | 19.0 |
| 16CNC6 | | <0.1 | 26.0 | 24.0 | 20.0 | 20.0 | 28.0 |
| 16CNM7 | | <0.1 | 68.0 | 126.0 | 134.0 | 115.0 | 210.0 |
| 16JNF2 | | <0.1 | 11.0 | 12.6 | 6.0 | 10.8 | 9.4 |
| 16JNG1 | | <0.1 | 8.0 | 14.8 | 7.0 | 12.3 | 11.0 |
| 16JNJ5 | | <0.1 | 19.0 | 14.8 | 25.0 | 23.0 | 27.0 |
| 16JNK2 | | <0.1 | 10.5 | 3.1 | 3.0 | 2.8 | 3.5 |
| Geometric Mean Titer | | <0.1 | 18.1 | 17.9 | 14.5 | 16.4 | 19.8 |
| 16CNM8 | 4 | <0.1 | 26.0 | 10.0 | 3.0 | 6.3 | 9.4 |
| 16CNO1 | | <0.1 | 24.0 | 14.1 | 6.0 | 11.5 | 23.0 |
| 16JNC1 | | <0.1 | 11.0 | 3.8 | 1.0 | 1.0 | 1.5 |
| 16JNJ3 | | <0.1 | 9.4 | 2.8 | 1.0 | 1.3 | 2.2 |
| 16JNO1 | | <0.1 | 113.0 | 31.0 | 14.0 | 9.0 | 8.8 |
| Geometric Mean Titer | | <0.1 | 23.6 | 8.6 | 3.0 | 3.9 | 5.7 |

The RP-rabies virus vaccine induces high serological anti-rabies titers when administered to cats as a single dose. Notably, the RFFIT titers in cats are higher than that observed for dogs vaccinated with a similar dose. The titer of 0.5 IU/mL by the RFFIT test is regarded as a protective titer however, it is known that cats with serological titers below this level are often protected from virulent challenge in long term immunity studies. All three groups vaccinated with the various doses of RP-rabies virus vaccine have higher group geometric mean anti-rabies virus RFFIT titers than the group vaccinated with a currently licensed commercial rabies product, which has a label indication for three years duration of immunity.

This initial study was followed up with a second study (currently on-going) that has resulted in analogous results, at least over the six month time period that has transpired.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

I claim:

1. A vaccine to aid in the prevention of disease due to rabies virus comprising a Venezuelan Equine Encephalitis (VEE) alphavirus RNA replicon particle (RP), and comprising a nucleotide sequence encoding a rabies virus antigen and a pharmaceutically acceptable carrier; wherein the nucleotide sequence encoding the rabies virus antigen comprises at least 85% sequence identity to the nucleotide sequence of SEQ ID NO: 1 or SEQ ID NO: 4.

2. The vaccine of claim 1, that comprises one or more additional alphavirus RNA replicon particles which encodes a second rabies virus antigen that originates from a different strain of rabies virus than the one that said rabies virus antigen originates from.

3. The vaccine of claim 2, wherein the second rabies virus antigen is a glycoprotein (G) or an antigenic fragment thereof.

4. The vaccine of claim 3, wherein the one or more additional alphavirus RNA replicon particles are VEE alphavirus RNA replicon particles.

5. The vaccine of claim 1, wherein the rabies virus antigen is a rabies virus glycoprotein (G) having an amino acid sequence comprising at least 95% identity with the amino acid sequence of SEQ ID NO: 2.

6. The vaccine of claim 5, wherein an antibody is induced in a mammal when said mammal is immunized with the vaccine.

7. The vaccine of claim 6, wherein the mammal is selected from the group consisting of a canine, a feline, an equine, a ferret, a sheep, and a bovine.

8. The vaccine of claim 1, that further comprises at least one non-rabies virus antigen for eliciting protective immunity to a non-rabies virus pathogen.

9. The vaccine of claim 1, that further comprises at least one recombinant vector that comprises a nucleotide sequence encoding at least one protein antigen or antigenic fragment thereof that originates from a non-rabies virus pathogen.

10. The vaccine of claim 1, that further comprises an alphavirus RNA replicon particle comprising a nucleotide sequence encoding at least one protein antigen or antigenic fragment thereof that originates from a non-rabies virus pathogen.

11. The vaccine of claim 1, that is a non-adjuvanted vaccine.

12. A method of immunizing a mammal against rabies virus comprising administering to the mammal an immunologically effective amount of the vaccine of claim 1.

13. The method of claim 12, wherein the mammal is selected from the group of a canine, a feline, and an equine.

14. The vaccine of claim 1, that comprises about $1 \times 10^6$ to about $1 \times 10^9$ RPs.

15. The vaccine of claim 11, that is a one dose vaccine.

16. The vaccine of claim 1, wherein the rabies virus antigen is a rabies virus glycoprotein (G) having an amino acid sequence of SEQ ID NO: 2.

17. The vaccine of claim 1, wherein the nucleotide sequence encoding the rabies virus antigen comprises the nucleotide sequence of SEQ ID NO: 1 or SEQ ID NO: 4.

18. The vaccine of claim 1, wherein the prevention of disease due to rabies virus in canines or felines comprises at least a three-year duration of immunity to said disease.

\* \* \* \* \*

UNITED STATES PATENT AND TRADEMARK OFFICE
CERTIFICATE OF CORRECTION

PATENT NO. : 11,992,526 B2
APPLICATION NO. : 16/759868
DATED : May 28, 2024
INVENTOR(S) : Ian Tarpey Page 1 of 1

It is certified that error appears in the above-identified patent and that said Letters Patent is hereby corrected as shown below:

In the Claims

In Column 23, Line 54 (Claim 1), delete ", and" to read:
-- (VEE) alphavirus RNA replicon particle (RP) comprising --

Signed and Sealed this
Eighteenth Day of February, 2025

Coke Morgan Stewart
*Acting Director of the United States Patent and Trademark Office*